United States Patent [19]

Matous et al.

[11] Patent Number: 5,578,585

[45] Date of Patent: Nov. 26, 1996

[54] PLEUROMUTILIN DERIVATIVE COMPLEXES

[75] Inventors: Heinrich F. Matous, Wörgl; Erich Zeisl, Jenbach, both of Austria

[73] Assignee: Biochemie Gesellschaft m.b.H., Tyrol, Austria

[21] Appl. No.: 402,272

[22] Filed: Mar. 10, 1995

Related U.S. Application Data

[63] Continuation of Ser. No. 918,514, Jul. 22, 1992, abandoned.

[30] Foreign Application Priority Data

Jul. 24, 1991 [AT] Austria .................................. 1477/91

[51] Int. Cl.[6] ........................... A01N 43/04; C07G 11/00; A61K 47/26; A23K 1/165
[52] U.S. Cl. .............. 514/58; 514/365; 514/54; 536/16.8; 536/103; 424/439; 424/442
[58] Field of Search ................................. 424/439, 442; 536/16.8, 103; 514/58, 365, 54

[56] References Cited

U.S. PATENT DOCUMENTS

| | | | |
|---|---|---|---|
| 3,987,194 | 10/1976 | Baughn et al. | 514/365 |
| 4,041,175 | 8/1977 | Brown et al. | 514/546 |
| 4,086,359 | 4/1978 | Dursch | 514/511 |
| 4,092,424 | 5/1978 | Branol et al. | 514/511 |
| 4,129,721 | 12/1978 | Michel et al. | 536/16.8 |
| 4,130,709 | 12/1978 | Nagarajan | 536/16.8 |
| 4,148,890 | 4/1979 | Czok et al. | 514/365 |
| 4,390,558 | 6/1983 | Ridgway et al. | 514/550 |
| 4,428,953 | 1/1984 | Berner et al. | 514/340 |
| 4,675,330 | 6/1987 | Berner et al. | 514/365 |
| 4,834,985 | 5/1989 | Elger et al. | 424/488 |
| 4,869,904 | 9/1989 | Uekama et al. | 514/58 |
| 5,007,966 | 4/1991 | Hedges et al. | 514/58 |
| 5,070,081 | 12/1991 | Majid et al. | 514/58 |

FOREIGN PATENT DOCUMENTS

| | | |
|---|---|---|
| 251459 | 1/1988 | European Pat. Off. . |
| 58-148816 | 9/1983 | Japan . |
| 59-010510 | 1/1984 | Japan . |

OTHER PUBLICATIONS

CRC Critical Reviews in Therapeutic Drug Carrier Systems, Vol. 3, issue 1, pp. 1–40 (1987) Uekama et al. (Authors).
Acta Pharm. Technol. 36, P5 (1990).
Int. J. Pharmaceutics, 67, 5–7 (1991).
Starke, 33 (1981), Nr.11, 387–390.
European Search Report (1988).

Primary Examiner—John Kight
Assistant Examiner—Louise N. Leary
Attorney, Agent, or Firm—Robert S. Honor; Melvyn M. Kassenoff; Thomas O. McGovern

[57] ABSTRACT

Complexes and pharmaceutical preparations containing complexes of the pleuromutilin derivative of formula I

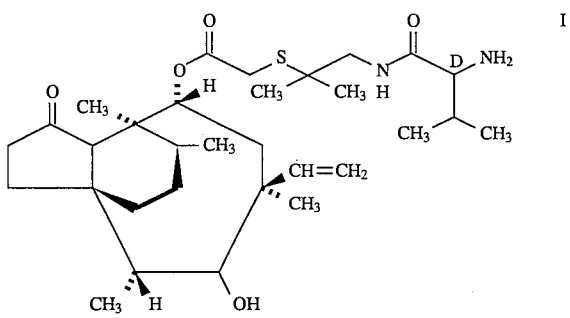

in free base or in acid addition or quaternary salt form and cyclodextrin are described.

They can be prepared by complexing the above pleuromutilin compound with an appropriate cyclodextrin.

They are indicated for use as pharmaceuticals, e.g. as antibiotics, especially in veterinary medicine, e.g. as feed additives.

22 Claims, No Drawings

PLEUROMUTILIN DERIVATIVE COMPLEXES

This is a continuation of application Ser. No. 07/918,514, filed Jul. 22, 1992, now abandoned.

The present invention relates to pleuromutilin derivatives. In particular it provides complexes of a pleuromutilin derivative and cyclodextrin and pharmaceutical preparations containing theses complexes.

Pleuromutilin derivatives are antibiotics with excellent micro-biological activity against a series of pathogenic microorganisms. In particular, the pleuromutilin derivative of formula I

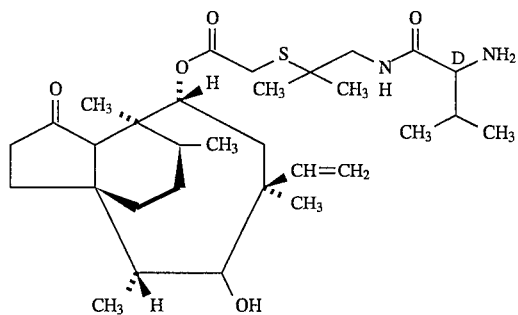

namely 14-O-[1-((D)-2-amino-3-methylbutyrylamino)-2-methylpropan-2-ylthioacetyl]mutilin, in free base or in acid addition or quaternary salt form, is highly effective against many gram-positive and gram-negative bacteria. Due to these properties the above compound may be employed as an antibiotic for the treatment of conditions induced by these pathogens, predominantly in veterinary medicine, for example on poultry, pigs, cattle, sheep and goats, especially in the treatment of respiratory tract disorders and dysentery.

Cyclodextrins are cyclic oligosaccharides made up of α-(1→4)-linked D-glucopyranose units, e.g., for α-, β and γ-cyclodextrin, respectively of 6, 7 or 8 units, which are described in detail in the literature, e.g. in J. Szejtli, *"Cyclodextrin Technology"*, Kluwer Academic Publishers (1988) and in D. Duchene *"Cyclodextrins and their Industrial Uses"*, Editions de Santé (1987). In the preparations according to the invention any cyclodextrin, e.g. α-, β- or γ-cyclodextrin or a derivative thereof may be used. It is preferable to use β- or γ-cyclodextrin or a derivative thereof, especially β- or γ-cyclodextrin. α-, β- and γ-cyclodextrins are non-toxic compounds which may be used without risk as pharmaceutical excipients for oral preparations. Moreover, in many countries β-cyclodextrin is also permissible as a food additive for human use.

Derivatives of cyclodextrin are for example ethers with lower alcohols, such as methylcyclodextrin or hydroxypropylcyclodextrin.

It is known from the literature that cyclodextrins can form inclusion compounds (inclusion complexes) with appropriate guest molecules, while the consequences on the effects obtained with the resultant complexes are difficult to predict. Based on the properties of the preparations according to the invention, it can be concluded that inclusion complexes similarly exist here. The observed desirable properties cannot be obtained solely from mere physical mixture.

It is observed that, surprisingly, with the compound of formula I in free base or in acid addition or quaternary salt form the formation of complexes with cyclodextrins results in a marked improvement of the properties of the resultant pharmaceutical preparations, particularly as regards stability in feed mixtures upon storage.

The compound of formula I is known from e.g. Sandoz U.S. Pat. No. 4,675,330 as Example 12 therein.

The preferred form of application of antibiotics to animals for therapeutic and prophylactic use is administration in the drinking water or feed. Whilst the compound of formula I in the form of its water-soluble hydrochloride may be administered easily and efficiently via the drinking water, application via the feed is difficult, because the substance is broken down very rapidly by constituents contained in conventional complete feed mixtures. However, the stability of ready feed/medicament mixtures is an essential requirement of practical application, since after stocks of such mixtures are produced it must be possible to stockpile them for at least several months.

A form of preparation is therefore desirable which has adequate stability in ready feed mixtures and can be administered orally to animals. Apart from the stability requirement of the feed, other essential requirements for application are good absorption, inexpensive production costs, a simple production process and acceptance by the treated animal.

It has now been found that preparations containing complexes of the compound of formula I in free base or in acid addition or quaternary salt form with a cyclodextrin fulfill these requirements to a large extent.

The invention thus concerns complexes of the pleuromutilin derivative of formula I as defined above in free base or in acid addition or quaternary salt form and a cyclodextrin, hereinafter briefly named "the complexes of the invention".

The invention further concerns pharmaceutical preparations comprising a complex of the pleuromutilin derivative of formula I as defined above in free base or in pharmaceutically acceptable acid addition or quaternary salt form and a cyclodextrin, together with at least one pharmaceutically acceptable carrier or diluent, hereinafter briefly named "the preparations of the invention".

The complexes of the invention can be prepared by a process which comprises complexing the compound of formula I in free base or in acid addition or quaternary salt form with an appropriate cyclodextrin.

The process of the invention is effected in conventional manner, preferably by contacting with an appropriate cyclodextrin under conditions suitable for complex formation. Various conventional method variants may be used thereby. It is possible to simply bring to dryness an aqueous solution of the compound and a cyclodextrin. To that effect lyophilization, spray-drying and/or evaporation can be employed. The complexes may further be obtained by moistening a physical mixture with water and kneading intensively. The complexes may also be produced by trituration of a such physical mixture of the two components, e.g. in a ball mill. Furthermore, it is possible to obtain the complexes by crystallization from a solution or a solvent mixture.

The ratio of compound of formula I to cyclodextrin may vary within a wide range. The molar ratio of components can e.g. be in the range of from about 1:0.25 to about 1:2, preferably a ratio of from about 1:0.75 to about 1:1.25 is employed, especially a ratio of about 1:1.

It is demonstrated by e.g. $^1$H-NMR spectroscopy (see under 3. below) that a chemical bond comprising at least hydrogen bonding or Van der Waals forces is formed between the compound of formula I and the cyclodextrin.

The preparations of the invention are manufactured in conventional manner, e.g. by a process which comprises mixing a complex of the pleuromutilin derivative of formula I as defined above in free base or in pharmaceutically acceptable acid addition or quaternary salt form and an appropriate cyclodextrin together with at least one pharmaceutically acceptable carrier or diluent.

The preparations of the invention can be manufactured with the compound of formula I in free base form or in water-soluble or water-insoluble salt form. Preferably the hydrochloride is employed.

The resultant inclusion complexes are described in more detail in the following experiments:
1. Phase-solubility Based on the phase-solubility diagram (see "Methods of investigating and preparing inclusion compounds and their industrial uses" in D. Duchene, *"Cyclodextrins and their Industrial Uses"*, Editions de Santé [1987]), the following types of inclusion compounds are obtained with the compound of formula I in the form of the base and

| β-cyclodextrin: | type $A_L$ |
| γ-cyclodextrin: | type $B_S$ |

For the compound of formula I the complex binding constant is $1050M^{-1}$ with β-cyclodextrin and $1400M^{-1}$ with γ-cyclodextrin.

2. Calorimetry

In micro-calorimetric examination of the complex of the compound of formula I in the form of the hydrochloride and β-cyclodextrin (L. E. Briggner et al. Microcalorimetric titration of β-cyclodextrine with adamantane-1-carboxylate, *Thermochimica Acta* 109 [1986] 139–143), a complex binding constant of $1004M^{-1}$ is obtained.

3. $^1$H-NMR-spectrum:

In the $^1$H-NMR-spectrum of a solution of the compound of formula I in the form of the hydrochloride and β-cyclodextrin in $D_2O$, marked changes in the signal position appear when compared with a pure solution of the compound of formula I, and these are attributable to the following functional groups:

| Proton no. | Compound of formula I (hydrochloride) (ppm) | Complex of β-cyclodextrin and compound of formula I (Example 3) (ppm) |
| --- | --- | --- |
| 16 | d 0.73 | s broad 0.69 |
| 17 | d 0.97 | s broad 0.96 |
| 18 | s 1.45 | s 1.49 |
| 8c | d 1.99 | d 1.72 |
| 4 | s 2.56 | s broad 2.58 |
| 20.20 | dd 5.24 | dd broad 5.35 |
| 19 | dd 6.37 | s broad ~6.5 |

4. Differential scanning calorimetry:

A preparation of γ-cyclodextrin and the compound of formula I in hydrochloride form corresponding to Example 1 shows in differential scanning calorimetry (10° K./min) an endothermic signal at 193° C.

5. Complex analysis:

Determination of the content of a preparation corresponding to Example 1 resulted in

| compound of formula I (hydrochloride) | 28.6% |
| $H_2O$ | 5.9% |

This content corresponds to a molar ratio of 1:1 of compound of formula I (HCl) to cyclodextrin.

In the following non-limitative Examples all temperatures are in degrees Centigrade:

EXAMPLE 1

5.76 g γ-cyclodextrin are dissolved in 18 ml of water under heating and 2.5 g compound of formula I (hydrochloride) are added. The solution is slowly cooled to 5° whilst stirring. The resultant white crystalline precipitate is decanted and dried in a vacuum drying chamber.

EXAMPLE 2

7.8 g β-cyclodextrin are dissolved in 60 ml of water under heating and 3.87 g compound of formula I (hydrochloride) are added. The solution is evaporated to dryness under reduced pressure. The dry residue is crushed through a 1 mm sieve.

EXAMPLE 3

The procedure is effected in a manner analogous to Example 2, with the exception that the solution is spray-dried at an air temperature of 180°.

EXAMPLE 4

The procedure is effected in a manner analogous to Example 2, with the exception that the solution is frozen to −40° during 3 hours and lyophilized.

EXAMPLE 5

2.9 g γ-cyclodextrin are dissolved in 10 ml of water under heating and 2.5 g of compound of formula I (hydrochloride) are added. The solution is spray-dried at an air temperature of 180°.

EXAMPLE 6

7.7 g compound of formula I (hydrochloride) are mixed with 15.5 g β-cyclodextrin and 15 ml of water are added in a kneading machine. The moist mass is kneaded intensively for 3 hours. It is subsequently dried in a vacuum drying chamber and crushed through a sieve.

EXAMPLE 7

3.5 g compound of formula I (hydrochloride) are mixed with 14.1 g β-cyclodextrin and ground in a ball mill for 6 hours.

EXAMPLE 8

Pre-mix

The preparations corresponding to Examples 1 to 7 are mixed with a meal feed mixture to a 2% pre-mix. The pre-mix is diluted to a concentration of 200 ppm of compound of formula I by mixing in a freefall mixer with further meal feed mixture.

EXAMPLE 9

Feed pellets

A feed mixture according to Example 8 is pressed into feed pellets using a appropriate pellet press and steam.

Some user-relevant properties of the preparations according to the invention are described in the following tests:
1. Feed stability As model feed a ready feed for piglets of the following composition is used:

| oats | 10.0% |
| corn | 29.0% |
| barley | 26.7% |
| wheat | 8.0% |
| soya scraps | 23.0% |
| calcium carbonate | 1.05% |
| dicalcium phosphate | 1.5% |
| iodized cattle salt | 0.25% |
| pre-mixture (mineral-vitamin) | 0.5% |

Various forms of the preparation are mixed with the ready feed in a concentration of 200 ppm of compound of formula I and stored for several weeks at 30°. Both the starting value of the fresh mixtures and the content values after storage for 2, 4 and 8 weeks are analysed by high pressure liquid chromatography (HPLC).

Table 1 shows the improvement in storage stability when using the complexes of the invention in a feed mixture, as compared with a corresponding preparation containing no cyclodextrin:

TABLE 1

| Feed mixture with | Content (in %) | | | |
| --- | --- | --- | --- | --- |
| | initial value | after 2 weeks | after 4 weeks | after 8 weeks |
| Compound of formula I (hydrochloride) alone | 100 | 15 | 8 | 6 |
| Complex of Example 3 | 100 | 89 | 87 | 90 |
| Complex of Example 6 | 100 | 91 | 92 | 88 |

For determination of the optimum ratio of compound of formula I to cyclodextrin, investigations are carried out using various concentrations of cyclodextrin. Results as regards stability in feed mixtures are summarized in Table 2 [in the first column "ratio" means the ratio of compound of formula I (hydrochloride) to β-cyclodextrin]:

TABLE 2

| Ratio | Content (in %) | | | |
| --- | --- | --- | --- | --- |
| | Initial value | after 1 month | after 2 months | after 3 months |
| 1:0 | 100 | 9 | 9 | 7 |
| 1:2 | 100 | 86 | 89 | 91 |
| 1:1 | 100 | 90 | 89 | 96 |
| 1:0.75 | 100 | 49 | 45 | 38 |
| 1:0.5 | 100 | 18 | 9 | 8 |
| 1:0.25 | 100 | 14 | 8 | 9 |

2. Oral absorption:

Absorption following administration to rats and pigs of 25 mg/kg body weight of a preparation according to Example 3 is tested and compared with pure compound of formula I (hydrochloride) in the drinking water. Blood samples are taken after a period of 24 hours and the concentration of active substance in plasma determined by microbiological analysis. The results in Table 3 show the absorption of the compound of formula I when administered in the form of a complex of the invention:

TABLE 3

| | $C_{max}$ (µg/ml) | | AUC (µg/ml.h) | |
| --- | --- | --- | --- | --- |
| | rat | pig | rat | pig |
| Compound of formula I (hydrochloride) alone | 8.6 | 1.2 | 139 | 21.4 |
| Complex according to Example 3 | 11.7 | 1.6 | 294 | 24.3 |

$C_{max}$ = maximum plasma concentration
AUC = area under curve

The complexes of the pleuromutilin derivative of formula I as defined above in free base or in pharmaceutically acceptable acid addition or quaternary salt form are therefore indicated for use as pharmaceuticals, particularly as antibiotics in the treatment of conditions induced by gram-positive and gram-negative bacteria, such as respiratory tract disorders and dysentery.

For this use the dosage to be employed will vary, of course, depending on the particular complex used, the mode of administration, the subject to be treated and the treatment desired. However, in general, satisfactory results are obtained when the complexes are administered at a daily dosage in e.g. pigs of from about 1 mg/kg to about 100 mg/kg body weight, conveniently from about 5 mg/kg to about 10 mg/kg, if desired given in divided dosages 2 to 4 times daily.

The complexes of the invention may be administered in similar manner to known standards for use in such indications. The complexes may be admixed with conventional pharmaceutically acceptable carriers and diluents and, optionally, further excipients, and administered e.g. orally in such forms as feed pellets and premixes.

The invention further includes a method of treatment of bacterial infections which comprises administering a therapeutically effective amount of a complex of the pleuromutilin derivative of formula I as defined above in free base or in pharmaceutically acceptable acid addition or quaternary salt form and a cyclodextrin to subjects, particularly to animals such as poultry, pigs, cattle, sheep and goats, in need of such treatment.

We claim:

1. A complex of the pleuromutilin derivative of formula I in free base or pharmaceutically acceptable acid addition or quaternary salt form and a cyclodextrin.

2. A pharmaceutical composition comprising a complex according to claim 1 and a pharmaceutically acceptable carrier or diluent therefor.

3. A complex according to claim 1 wherein the pleuromutilin derivative of formula I is in the form of the hydrochloride.

4. A complex according to claim 1 wherein the cyclodextrin is β- or γ-cyclodextrin.

5. A complex according to claim 1 wherein the molar ratio of pleuromutilin derivative to cyclodextrin is from 1:0.25 to 1:2.

6. A complex according to claim 1 wherein the molar ratio of pleuromutilin derivative to cyclodextrin is from 1:0.75 to 1:1.25.

7. A complex according to claim 1 wherein the molar ratio of pleuromutilin derivative to cyclodextrin is 1:1.

8. A method of treating a bacterial infection in an animal which comprises administering a therapeutically effective amount of a complex according to claim 1 to an animal in need of such treatment.

9. A complex according to claim 1 in which the pleuromutilin of formula I is in free base or pharmaceutically acceptable acid addition salt form.

10. A pharmaceutical preparation according to claim 2, wherein the cyclodextrin is β or γ-cyclodextrin.

11. A pharmaceutical preparation according to claim 2 wherein the molar ratio of pleuromutilin derivative to cyclodextrin is 1:0.25 to 1:2.

12. A pharmaceutical preparation according to claim 2 wherein the molar ratio of pleuromutilin derivative to cyclodextrin is 1:0.75 to 1:1.25.

13. A pharmaceutical preparation according to claim 2 wherein the molar ratio of pleuromutilin derivative to cyclodextrin is 1:1.

14. A method according to claim 8 in which the animal is selected from poultry, pigs, cattle, sheep and goats.

15. A method according to claim 8 in which the bacterial infection is a respiratory tract disorder or dysentery.

16. A ready feed-medicament preparation comprising a therapeutically effective amount of a complex according to claim 1 and an animal feed carrier therefor.

17. A complex according to claim 1 of the pleuromutilin derivative of formula I

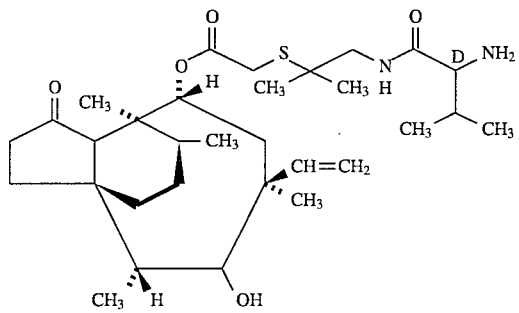

in pharmaceutically acceptable acid addition salt form and a β or γ cyclodextrin, wherein the molar ratio of pleuromutilin derivative to β or γ cyclodextrin is 1:0.25 to 1:2.

18. A complex according to claim 17 wherein the molar ratio of pleuromutilin derivative to β or γ cyclodextrin is 1:0.75 to 1:1.25.

19. A complex according to claim 17 wherein the molar ratio of pleuromutilin derivative to β or γ cyclodextrin is 1:1.

20. A ready feed medicament preparation comprising a therapeutically effective amount of a complex according to claim 17 and an animal feed carrier therefor.

21. A ready feed medicament preparation comprising a therapeutically effective amount of a complex according to claim 18 and an animal feed carrier therefor.

22. A ready feed medicament preparation comprising a therapeutically effective amount of a complex according claim 19 and an animal feed carrier therefor.

* * * * *